(12) United States Patent
Jaklinski et al.

(10) Patent No.: US 7,744,370 B2
(45) Date of Patent: Jun. 29, 2010

(54) DENTAL DEVICE FOR INSERTION OF A CROWN

(76) Inventors: Jeffrey P. Jaklinski, 3435 Boone Ave. Southwest, Wyoming, MI (US) 49519; John Lechel, 4277 Glasgow Ct., Wayland, MI (US) 49348

( * ) Notice: Subject to any disclaimer, the term of this patent is extended or adjusted under 35 U.S.C. 154(b) by 349 days.

(21) Appl. No.: 11/878,451

(22) Filed: Jul. 24, 2007

(65) Prior Publication Data

US 2008/0026345 A1  Jan. 31, 2008

Related U.S. Application Data

(60) Provisional application No. 60/832,961, filed on Jul. 25, 2006.

(51) Int. Cl.
*A61C 9/00* (2006.01)
(52) U.S. Cl. .......................................... 433/71; 433/70
(58) Field of Classification Search .................. 433/70, 433/71, 218
See application file for complete search history.

(56) References Cited

U.S. PATENT DOCUMENTS

| | | | |
|---|---|---|---|
| 2,183,624 A | 12/1939 | Schwartz | |
| 2,404,683 A | 7/1946 | Barishman | |
| 2,633,637 A | 4/1953 | Lucia | |
| 2,674,797 A | 4/1954 | Skinner | |
| 3,118,230 A | 1/1964 | Trapozzano | |
| 3,126,631 A | 3/1964 | McCarthy et al. | |
| 3,421,223 A | 1/1969 | Stark | |
| 3,604,116 A | 9/1971 | Shpuntoff | |
| 3,959,881 A | 6/1976 | Kokal, Jr. | |
| 4,541,803 A | 9/1985 | Adler | |
| 4,547,155 A | 10/1985 | Adler | |
| 4,676,748 A | 6/1987 | Pietkivitch | |
| 4,708,649 A | 11/1987 | Millstein | |
| 5,226,813 A | 7/1993 | Shew | |
| 6,464,103 B1 * | 10/2002 | Schroeder | 221/47 |
| 6,932,602 B2 | 8/2005 | Hamilton et al. | |
| 2006/0063125 A1 | 3/2006 | Hamilton et al. | |

FOREIGN PATENT DOCUMENTS

GB  2250922  6/1992

* cited by examiner

*Primary Examiner*—Cris L Rodriguez
*Assistant Examiner*—Eric Rosen
(74) *Attorney, Agent, or Firm*—Richard C. Litman

(57) ABSTRACT

The dental device for insertion of a crown is a tool for marking an occlusally reduced tooth prior to application of a crown thereon, and for testing whether the tooth has been sufficiently reduced for proper application of the crown. The dental device includes a marking portion frangibly joined to a resistance testing portion. The marking portion includes a marking layer formed of a transferable material so that, following occlusal reduction of the tooth, the marking portion is separated from the resistance testing portion, and the marking layer is positioned against an upper surface of the tooth. The patient bites down on the marking layer to mark raised regions of the upper surface of the tooth, and subsequently bites down on the resistance testing portion, to test if the tooth has been sufficiently reduced for application of a crown thereon.

10 Claims, 5 Drawing Sheets

DENTAL DEVICE FOR INSERTION OF A CROWN

CROSS-REFERENCE TO RELATED APPLICATION

This application claims the benefit of U.S. Provisional Patent Application Ser. No. 60/832,961, filed Jul. 25, 2006.

BACKGROUND OF THE INVENTION

1. Field of the Invention

The present invention relates to dental appliances, and particularly to a dental device for insertion of a crown.

2. Description of the Related Art

Prior to application of an artificial dental article, such as a crown, to a tooth, the tooth must often be occlusally reduced, typically through grinding with a drill or the like. A full gold crown, for example, typically has a thickness between 0.5 and one millimeter, thus requiring the upper surface of the tooth to be occlusally reduced by a matching thickness so that the patient's ability to bite and chew remains unchanged following the dental procedure.

If the tooth to be occlusally reduced is a lower tooth, the upper surface of the tooth includes raised regions, which mate with and engage corresponding raised regions of a vertically opposed upper tooth. Following occlusal reduction, the upper surface of the tooth still includes raised regions and, in order to properly form and position the crown over the occlusally reduced tooth, the dental practitioner must be aware of the location and contouring of these raised regions. The raised regions are typically marked with a non-toxic material, such as resin, wax, charcoal, carbon or the like Once the raised regions have been marked for formation and fitting of the crown, the dental practitioner must make sure that the upper surface of the tooth has been reduced enough for proper placement of the crown; i.e., once the crown has been applied to the occlusally reduced tooth, the upper surface of the crown should be positioned at a height identical to that of the surface of the tooth prior to reduction.

In order to test whether the tooth has been properly reduced in height, dental practitioners often use what is commonly referred to as "the tug test", which involves the positioning of a frictional material between the occlusally reduced tooth and the corresponding vertically opposed tooth, and then pulling or "tugging" on the frictional material to measure the amount of resistance to removal the frictional material provides. When the patient bites down on the frictional material, the frictional material should offer a slight resistance to removal, which an experienced dental practitioner can measure in order to determine if the tooth has been reduced enough for proper application of the crown. Thus, a dental device for insertion of a crown and method of using the same solving the aforementioned problems is desired.

SUMMARY OF THE INVENTION

The dental device for insertion of a crown is a tool for marking an occlusally reduced tooth prior to application of a crown thereon, and for testing whether the tooth has been sufficiently reduced for proper application of the crown. The dental device includes a marking portion frangibly joined to a resistance testing portion. Preferably, a base layer, formed from a material that frictionally engages the tooth, such as rubber, is provided. The base layer is longitudinally divided into the marking portion and the resistance testing portion, with the marking portion being frangible from the resistance testing portion. Preferably, a slot is formed substantially centrally in the base layer that extends in the lateral direction, forming the frangible connection.

The marking portion includes a marking layer formed of a transferable material so that, following occlusal reduction of the tooth, the marking portion is separated from the resistance testing portion, and the marking layer is positioned against an upper surface of the tooth. The patient applies pressure to the marking portion by biting on the marking portion, which is positioned between the occlusally reduced tooth and a vertically opposed tooth. This application of pressure transfers the transferable medium of the marking layer to raised regions of the upper surface of the tooth, allowing the dental practitioner to properly fit the crown.

Following marking of the tooth, the marking portion is removed from the mouth of the patient, and the resistance testing portion is inserted between the occlusally reduced tooth and the vertically opposed tooth. The patient bites down on the resistance testing portion, and the resistance testing portion frictionally engages both the upper surface of the occlusally reduced tooth and the vertically opposed tooth. By attempting to remove the resistance testing portion, and measuring the amount of resistance to removal the frictional engagement provides, the dental practitioner is able to test if the occlusally reduced tooth has been sufficiently reduced for application of a crown thereon.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed towards a dental device 10, which is used for the formation and application of a crown or other dental article. The dental device 10 is a tool for dental practitioners to mark an occlusally reduced tooth prior to application of a crown thereon, and for subsequently testing whether the tooth has been sufficiently reduced for proper application of the crown.

Figure 1:
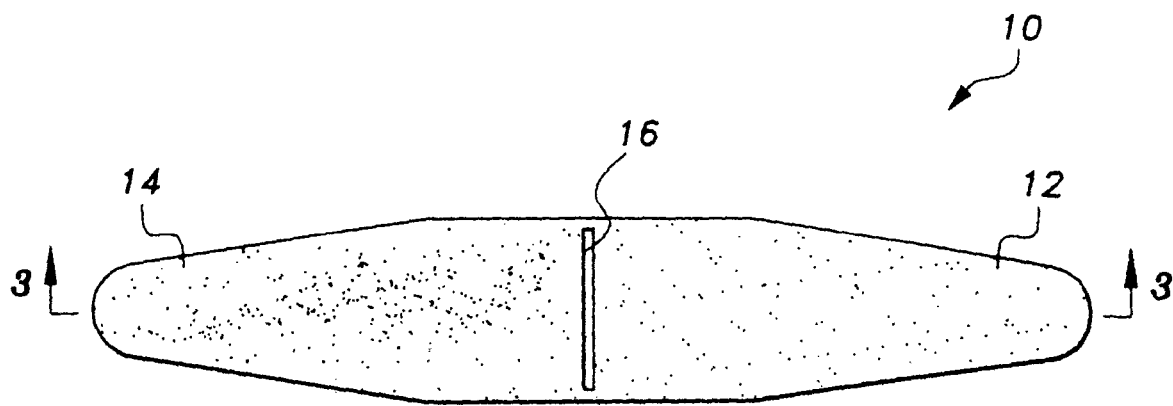
FIG. 1 is a plan view of a dental device for insertion of a crown according to the present invention.
Figure 2:
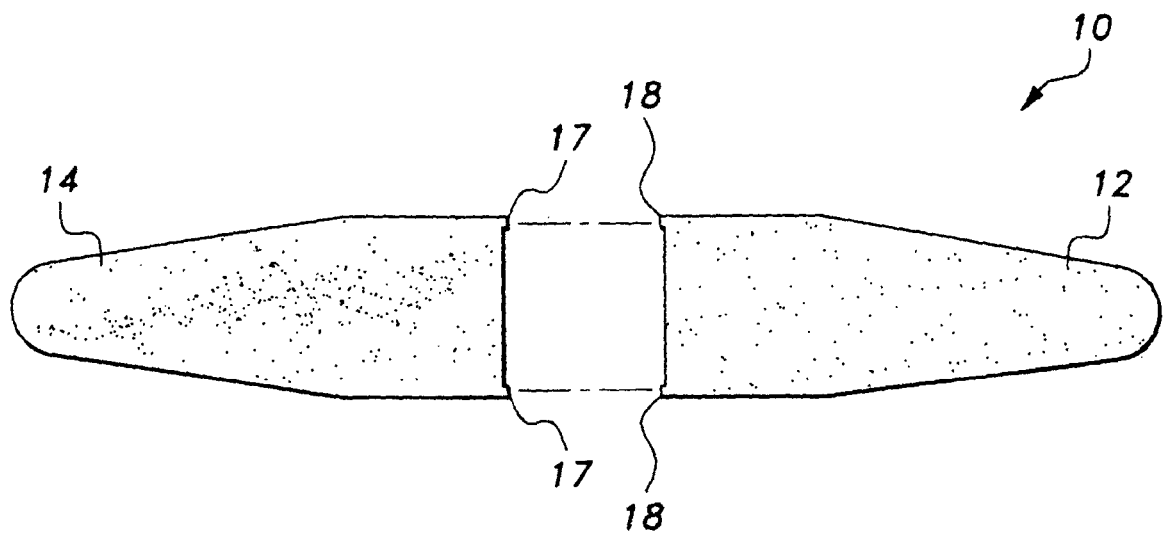
FIG. 2 is an exploded plan view of the dental device for insertion of a crown according to the present invention.
Figure 3:
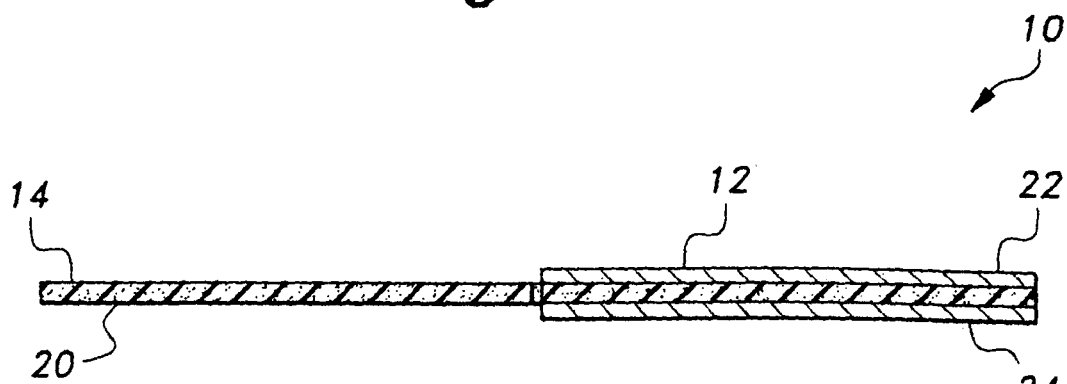
FIG. 3 is a section view taken along lines 3-3 of FIG. 1.

As best shown in FIGS. 1-3, the dental device 10 includes a marking portion 12, which is frangibly joined to a resistance testing portion 14. In the preferred embodiment, the dental device 10 extends in the longitudinal direction with a length of approximately fifty millimeters. The maximum length in the lateral direction is preferably approximately nine millimeters. The exemplary dimensions given above are selected for application to a single occlusally reduced tooth and provide sufficient length so that the device 10 may be gripped by the dental practitioner.

Preferably, as best shown in FIG. 3, dental device 10 includes a base layer 20 or substrate, which is formed from a flexible, preferably resilient material, such as natural or synthetic rubber or other elastomeric polymer, that can frictionally engage the teeth. A suitable material is a styrene-ethylene/butylene-styrene (SEBS) or styrene-ethylene/propylene-styrene (SEPS) copolymer marketed as Kraton® G-2705 (Kraton is a registered trademark of Shell Oil Company of Houston, Tex.). It should be understood that base layer 20 may be formed from any suitable flexible and frictional material that is safe, hygienic, non-toxic and suitable for dental purposes.

The base layer 20 is longitudinally divided into the marking portion 12 and the resistance testing portion 14, with the device 10 being frangible so that the marking portion 12 is separable from the resistance testing portion 14. As shown in FIG. 1, a slot 16 may be formed that extends in the lateral direction substantially centrally through the base layer 20, forming the frangible connection. When the dental practitioner chooses to separate the marking portion 12 from the resistance testing portion 14, the resistance testing portion 14 is torn from the marking portion 12 along the slot 16, as shown in FIG. 2. The separation will result in the formation of small tabs 17 on the resistance testing portion 14, and a complementary pair of small tabs 18 formed on the marking portion 12. Tabs 17, 18 preferably each have a width, measured in the lateral direction, of approximately 0.25 mm. Although shown in the drawings as having a single slot 16, it should be understood that marking layer 12 may be frangibly joined to resistance testing portion 14 in any suitable manner, such as by a perforated connection, a score line, etc.

As shown in FIG. 3, the marking portion 12 includes at least one marking layer 24 formed from a transferable material such as wax, carbon, charcoal, chalk or any other marking substance safe for oral use, which is coated on a first surface thereof. A second marking layer 22 may optionally be coated on a second surface opposite the first surface so that two teeth may be marked simultaneously (as will be described below). A suitable transferable material or transferable medium is Kontakt liquid, made by American Dental Supply, Inc. of Easton, Pa.

Figure 4:
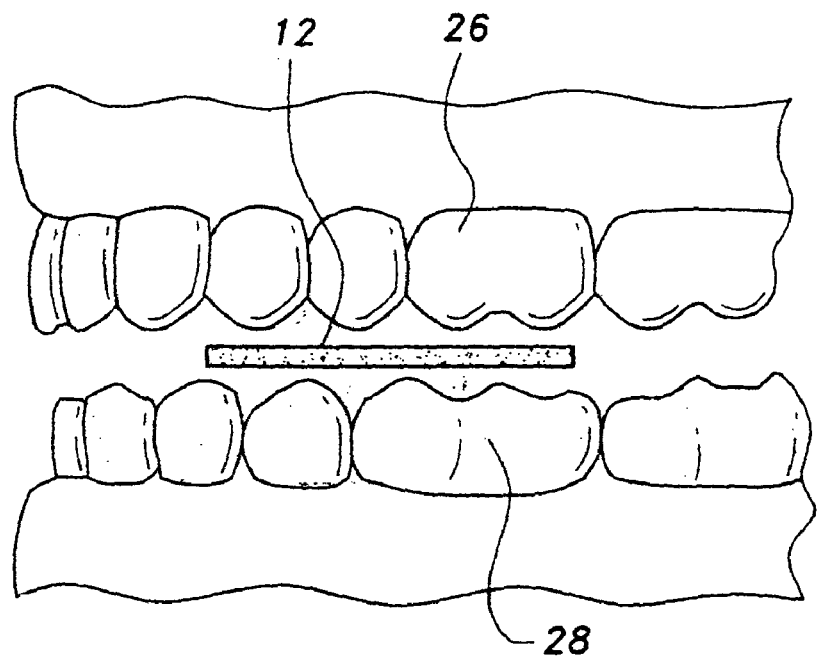
FIG. 4 is a side environmental view of a marking portion of the dental device for insertion of a crown according to the present invention being inserted between an occlusally reduced tooth and a vertically opposed tooth.

In FIG. 4, the tooth to which the crown will be applied is referred to generally as 28. Tooth 28 has been occlusally reduced for proper fitting and application of the crown thereon. Following occlusal reduction of tooth 28, the marking portion 12 is separated from the resistance testing portion 14, and the marking portion 12 is inserted into the patient's mouth. The marking portion 12 is positioned between the occlusally reduced tooth 28 and a vertically opposed tooth 26. The marking portion 12 is positioned so that the marking layer 24 contacts the occlusally reduced upper surface 29 of the tooth 28 (the upper surface 29 is best shown in FIG. 7).

Figure 5:
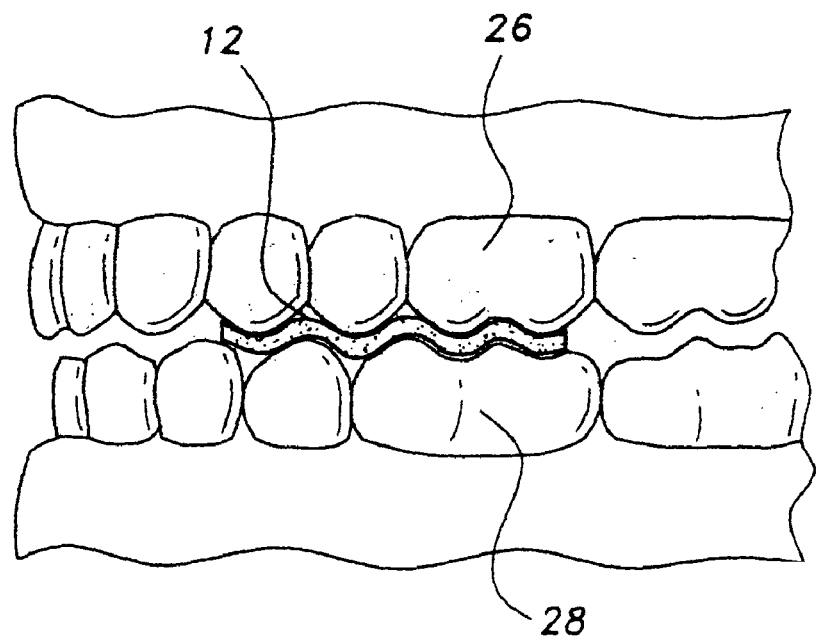
FIG. 5 is a side environmental view of the marking portion of the dental device for insertion of a crown according to the present invention being bitten between the occlusally reduced tooth and the vertically opposed tooth.
Figure 6:
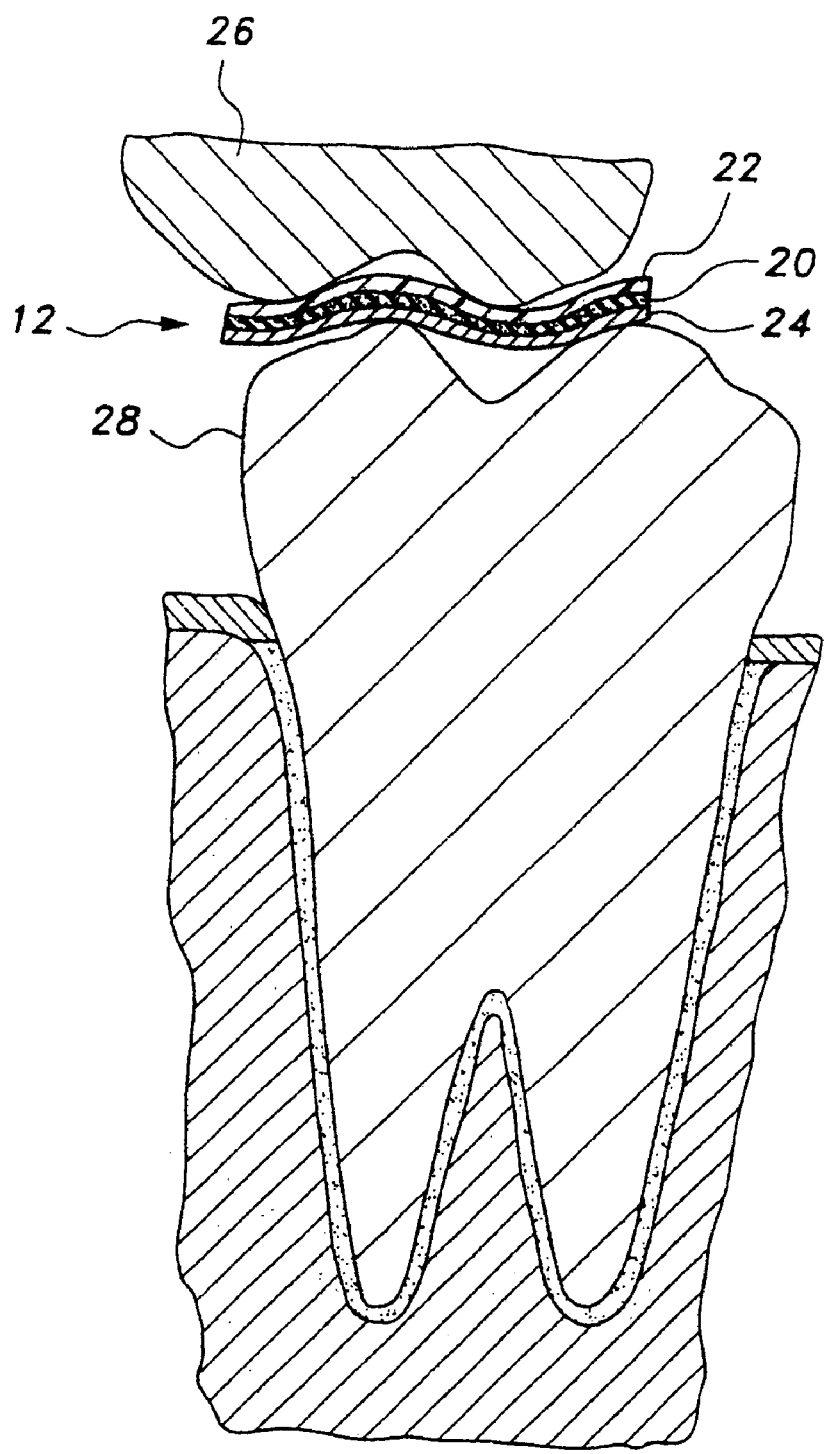
FIG. 6 is an enlarged cross-sectional side environmental view of the marking portion of the dental device for insertion of a crown according to the present invention being bitten between the occlusally reduced tooth and the vertically opposed tooth, as in FIG. 5.

In order to properly shape and apply the crown, the dental practitioner must be aware of the positioning and contouring of the raised regions of upper surface 29. In order to mark these raised regions, the patient applies pressure to the marking portion 12 by biting on the marking portion 12, which is placed between the occlusally reduced tooth 28 and the vertically opposed tooth 26, as shown in FIGS. 5 and 6. This application of pressure transfers the transferable medium of the marking layer 24 to the raised regions of the upper surface 29 of the tooth 28, allowing the dental practitioner to properly fit the crown. The dental practitioner may further wish to mark the raised regions of the vertically opposed tooth 26, and the usage of second marking layer 22 allows for the creation of these corresponding markings (as best shown in FIG. 6).

Figure 7:
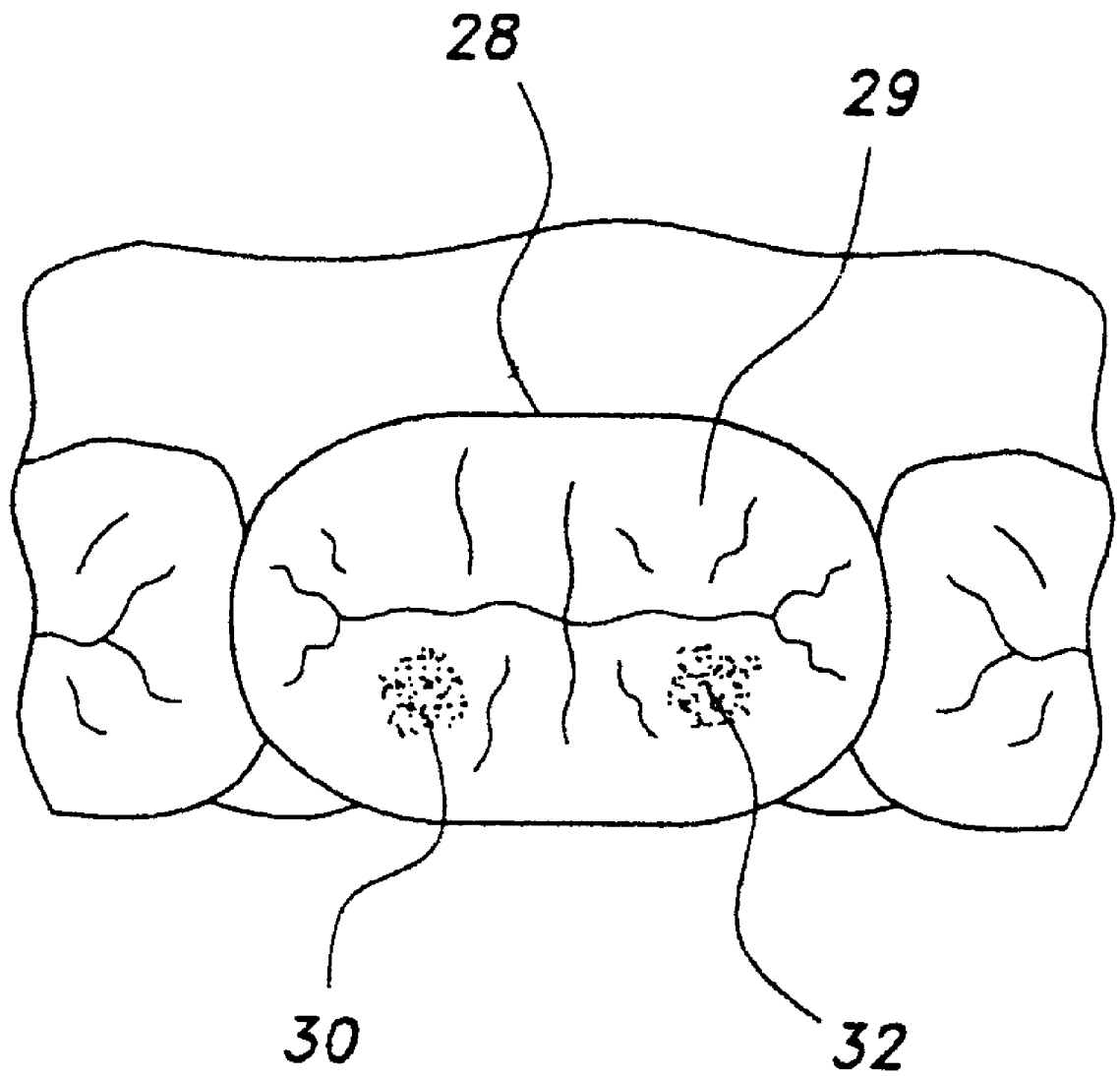
FIG. 7 is an environmental plan view showing the marking of raised regions of the occlusally reduced tooth following application of the marking portion of the dental device of the present invention, as in FIGS. 5 and 6.

FIG. 7 illustrates the formation of markings 30, 32 on the raised regions of upper surface 29. The marking material forming marking layers 22, 24 preferably has a color that contrasts with the surface of the teeth. The marking or coloring of the raised regions indicates the location of the raised regions, and further indicates to the dental practitioner the locations where the greatest pressure during biting or chewing occurs. When the patient bites down on marking portion 12, the intensity of markings 30, 32 will give the dental practitioner an indication of where the greatest pressure during biting occurs; i.e., a large amount of pressure will result in the transfer of a larger amount of the transferable medium, producing a darker mark, and a lesser amount of pressure will result in the transfer of a lesser amount of the transferable medium, producing a lighter mark.

Figure 8:
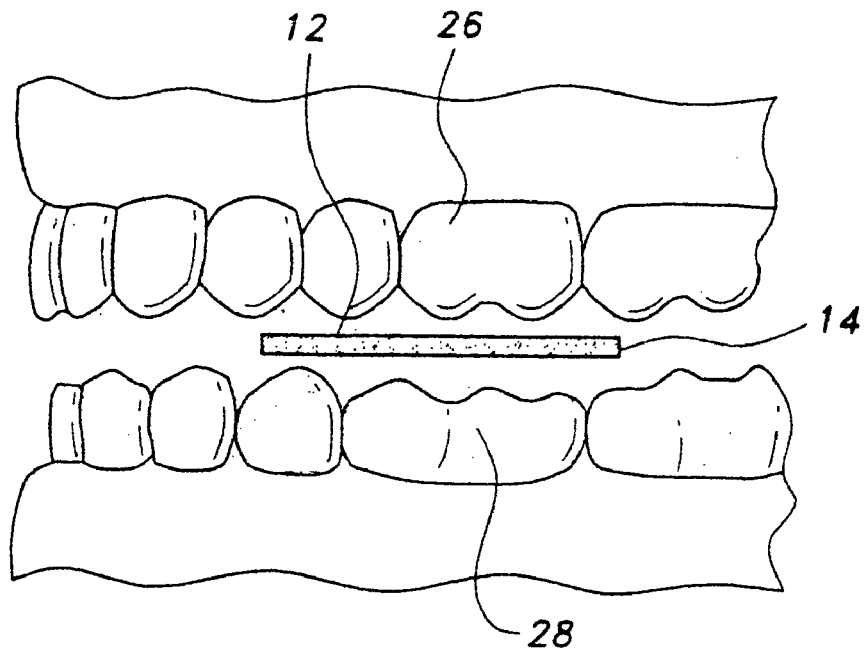
FIG. 8 is a side environmental view of a resistance testing portion of the dental device for insertion of a crown according to the present invention being inserted between the occlusally reduced tooth and the vertically opposed tooth.
Figure 9:
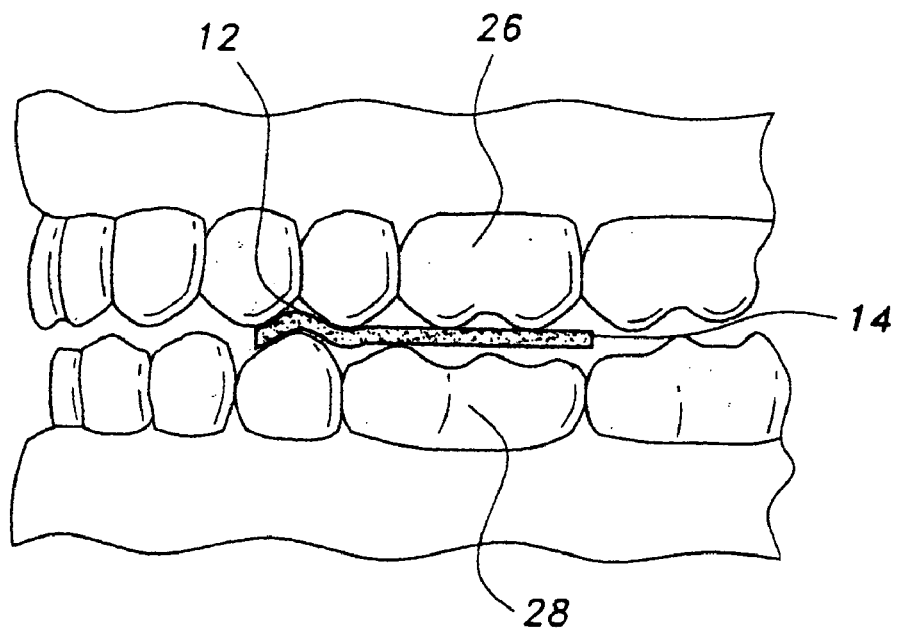
FIG. 9 is a side environmental view of the resistance testing portion of the dental device for insertion of a crown according to the present invention being bitten between the occlusally reduced tooth and the vertically opposed tooth.

Following marking of the tooth or teeth, the marking portion 12 is removed from the mouth of the patient, and the resistance testing portion 14 is inserted between the occlusally reduced tooth 28 and the vertically opposed tooth 26, as shown in FIG. 8. As illustrated in FIG. 9, the patient bites down on the resistance testing portion 14 in a manner similar to that shown in FIGS. 5 and 6 with respect to the marking portion 12, and the resistance testing portion 14 frictionally engages both the upper surface 29 of the occlusally reduced tooth 28 and the lower surface of the vertically opposed tooth 26. By attempting to remove the resistance testing portion 14 from between teeth 26, 28, and measuring the amount of resistance to removal the frictional engagement provides, the dental practitioner is able to test if the occlusally reduced tooth 28 has been sufficiently reduced for application of a crown thereon. As described above, with regard to the "tug test", when the patient bites down on the resistance testing portion 14, the frictionally engaging material of base layer 20 should offer a slight resistance to removal from between the patient's teeth if the tooth has been sufficiently reduced. The dental practitioner can measure the degree of this resistance in order to determine if the tooth 28 has been reduced enough for proper application of the crown.

Dental device 10 provides both a marking portion 12 and a resistance testing portion 14, manufactured as an integrally formed unit, the device 10 being frangible such that the portions 12 and 14 are selectively separable from one another. Device 10 is portable, may be easily stored, and is preferably formed from hygienic and disposable materials.

It is to be understood that the present invention is not limited to the embodiments described above, but encompasses any and all embodiments within the scope of the following claims.

We claim:

1. A dental device for insertion of a crown, consisting essentially of:
   a substantially planar elongated base layer having a marking portion and a resistance testing portion, separated by a frangible joint, the base layer having opposed first and second surfaces, wherein said marking portion and said resistance testing portion each have a longitudinally opposed end located opposite the frangible joint and a common longitudinal axis traversing the ends and the frangible joint, said marking portion and said resistance testing portion being substantially symmetrically configured about the frangible joint located at the approximate midpoint of the base layer; and
   a first marking layer formed from a transferable medium coated on the first surface of the marking portion of the base layer, the first marking layer being adapted for positioning against an upper surface of an occlusally reduced tooth to mark raised regions of the upper surface, the resistance testing portion being adapted for positioning between the occlusally reduced tooth and a vertically opposed tooth following marking of the raised regions, the resistance testing portion being adapted for frictionally engaging the occlusally reduced tooth and the vertically opposed tooth in order to measure the degree of occlusal reduction of the occlusally reduced tooth.

2. The dental device for insertion of a crown as recited in claim 1, wherein the frangible joint is a slot formed through said base layer at the juncture of said marking portion and said resistance testing portion, said slot extending along a substantially lateral direction orthogonal to the longitudinal axis.

3. The dental device for insertion of a crown as recited in claim 1, wherein said base layer is formed from a flexible material.

4. The dental device for insertion of a crown as recited in claim 1, wherein the transferable medium of the first marking layer is selected from the group consisting of resin, wax, carbon, charcoal, chalk and combinations thereof.

5. The dental device for insertion of a crown as recited in claim 1, further comprising a second marking layer coated on the second surface of the marking portion, the second marking layer being formed from a transferable medium.

6. The dental device for insertion of a crown as recited in claim 5, wherein the transferable medium of the first marking layer and the transferable medium of the second marking layer are selected from the group consisting of resin, wax, carbon, charcoal, chalk and combinations thereof.

7. The dental device for insertion of a crown according to claim 1, wherein said base layer is made from an elastomeric polymer.

8. The dental device for insertion of a crown according to claim 1, wherein said base layer is made from an elastomeric material selected from the group consisting of natural rubber, synthetic rubber, and an elastomeric block copolymer.

9. A method of using a dental device for the insertion of a crown, comprising the steps of:
   providing a dental device, said dental device consisting essentially of a substantially planar elongated base layer having a resistance testing portion being substantially configured and frangibly joined to a marking portion by a frangible joint, the marking portion having at least one marking layer formed on a surface thereof, the marking layer being formed of a transferable medium coated on the marking portion, the base layer having opposed first and second surfaces, wherein said marking portion and said resistance testing portion each have a longitudinally opposed end opposite the frangible joint and a common longitudinal axis traversing the ends and the frangible joint, said marking portion and said resistance testing portion being substantially symmetrically configured about the frangible joint located at the approximate midpoint of the base layer;
   occlusally reducing a tooth to form an occlusally reduced tooth having an occlusally reduced upper surface;
   separating the resistance testing portion of the dental device from the marking portion;
   positioning the marking portion between the occlusally reduced tooth and a vertically opposed tooth, the at least one marking layer being positioned against the occlusally reduced upper surface;
   applying pressure to the marking portion so that the transferable medium is transferred to at least one raised region of the occlusally reduced upper surface to mark the at least one raised region for fitting of a crown on the occlusally reduced tooth;
   removing the marking portion from between the occlusally reduced tooth and the vertically opposed tooth;
   positioning the resistance testing portion between the occlusally reduced tooth and the vertically opposed tooth;
   applying pressure to the resistance testing portion so that the resistance testing portion frictionally engages the vertically opposed tooth and the occlusally reduced tooth;
   measuring the frictional resistance to removal of the resistance testing portion from between the occlusally reduced tooth and the vertically opposed tooth to test whether the occlusally reduced upper surface has been properly occlusally reduced for application of the crown; and
   applying a crown to the occlusally reduced tooth.

10. The method of using a dental device for the insertion of a crown as recited in claim 9, further comprising the steps of:
   providing a second marking layer formed on the marking portion; and
   applying pressure to the second marking portion so that a transferable medium thereof is transferred to a surface of the vertically opposed tooth.

* * * * *